(12) United States Patent
Takahashi et al.

(10) Patent No.: US 10,814,045 B2
(45) Date of Patent: Oct. 27, 2020

(54) DEVICES AND METHODS FOR ANEURYSM TREATMENT

(71) Applicant: BALT USA, Irvine, CA (US)

(72) Inventors: Randall Takahashi, Mission Viejo, CA (US); David Ferrera, Coto de Caza, CA (US)

(73) Assignee: BALT USA, Irvine, CA (US)

( * ) Notice: Subject to any disclaimer, the term of this patent is extended or adjusted under 35 U.S.C. 154(b) by 270 days.

(21) Appl. No.: 15/771,187

(22) PCT Filed: Oct. 30, 2015

(86) PCT No.: PCT/US2015/058215
§ 371 (c)(1),
(2) Date: Jul. 2, 2018

(87) PCT Pub. No.: WO2017/074411
PCT Pub. Date: May 4, 2017

(65) Prior Publication Data
US 2019/0201592 A1   Jul. 4, 2019

(51) Int. Cl.
*A61F 2/958* (2013.01)
*A61L 31/14* (2006.01)
*A61B 17/12* (2006.01)
*A61L 31/08* (2006.01)
*A61B 5/026* (2006.01)
(Continued)

(52) U.S. Cl.
CPC ............ *A61L 31/14* (2013.01); *A61B 5/0263* (2013.01); *A61B 5/4848* (2013.01); *A61B 17/1214* (2013.01); *A61B 17/1227* (2013.01); *A61B 17/12118* (2013.01); *A61B 17/12145* (2013.01); *A61F 2/95* (2013.01); *A61L 31/022* (2013.01); *A61L 31/088* (2013.01); *A61B 2017/00867* (2013.01); *A61B 2017/00911* (2013.01); *A61B 2505/05* (2013.01); *A61F 2002/823* (2013.01); *A61F 2210/0076* (2013.01); *A61F 2250/0098* (2013.01); *A61L 2420/02* (2013.01); *A61L 2430/36* (2013.01)

(58) Field of Classification Search
CPC .... A61F 2/95; A61F 2/07; A61F 2/954; A61F 2/958; A61F 2/966; A61F 2/06; A61B 17/12; A61B 17/122; A61B 17/12118; A61B 17/12145
See application file for complete search history.

(56) References Cited

U.S. PATENT DOCUMENTS 6,013,855 A  *  1/2000  McPherson ............. A61L 27/34
                                                          427/2.24
9,795,388 B1 * 10/2017  Evans ................. A61B 17/1214
(Continued)

*Primary Examiner* — Vi X Nguyen
(74) *Attorney, Agent, or Firm* — PATNSTR®, APC; Peter Jon Gluck, Esq.

(57) ABSTRACT

The invention provides devices and methods for aneurysm treatment using a material that minimizes susceptibility artifacts in MRA images. Since images are not obscured by susceptibility artifacts associated with the aneurysm treatment device, those images are useful and reliable for evaluating the success of treatment. The material is preferably a non-ferromagnetic metal alloy and may include one or a combination of cobalt, nickel, chromium, and molybdenum. In certain embodiments, the material is a 35Cobalt-35Nickel-20Chromium-10Molybdenum-Low Titanium alloy medical-grade material.

1 Claim, 15 Drawing Sheets

(51) Int. Cl.
*A61B 5/00* (2006.01)
*A61B 17/122* (2006.01)
*A61F 2/95* (2013.01)
*A61L 31/02* (2006.01)
*A61B 17/00* (2006.01)
*A61F 2/82* (2013.01)

(56) References Cited

U.S. PATENT DOCUMENTS

2003/0070469 A1* 4/2003 Kokish .................. A61F 2/958
    72/402
2007/0032862 A1* 2/2007 Weber ...................... A61F 2/82
    623/1.34

* cited by examiner

DEVICES AND METHODS FOR ANEURYSM TREATMENT

FIELD OF THE INVENTION

The invention relates to magnetic-resonance compatible devices and materials for cerebral aneurysm repair.

BACKGROUND

A brain aneurysm is a swollen blood vessel in a person's brain that can grow and rupture. Before an aneurysm ruptures, the person may suffer severe headaches, nausea, vision impairment, vomiting, and loss of consciousness. Ruptured aneurysms are treated to prevent re-bleeding, and clipping is one such treatment. In the clipping treatment, part of the skull bone is temporarily removed and the base of the aneurysm is clipped to stop bleeding. However, clipping is invasive, difficult to perform, and brings a risk of infection.

A less invasive option is vascular embolization, in which implants such as metal coils are placed in the aneurysm to create blood stasis and promote blood clotting, which physically blocks the flow of blood into the aneurysm. In coil embolization, a microcatheter is used to guide the embolization coil to the aneurysm under x-ray or digital subtraction angiography (DSA) guidance. A pusher wire attached to the delivery device then delivers the coil into the aneurysm.

Unfortunately, the treatment is not always a complete success. Large aneurysms are difficult to fully embolize. Also, the coils can move or displace in time after embolization in a phenomenon known as coil compaction, sometimes resulting in a hemorrhage or re-bleeding if previously hemorrhaged. In addition, the coils and the blood clot formed to heal the aneurysm can become dislodged leading to cerebral infarction.

After treating an aneurysm, the treatment site can be examined by imaging to determine if the treatment performed is stable or if further treatment is required. Although digital subtraction angiography (DSA) is the gold standard imaging modality, it is a less-invasive procedure that exposes the patient to ionizing radiation and possible morbidity. Computed tomography (CT) angiography may be used to detect aneurysms. However, CT scans may exhibit streaks and shadows adjacent to areas of high density such as bones because the high density anatomy preferentially absorbs lower-energy photons in a phenomenon known as beam-hardening.

Magnetic resonance angiography (MRA) is a promising imaging modality for follow-up monitoring of aneurysm treatment due to its non-invasive nature, high resolution, and sensitivity. However, coils or dips are associated with visual artifacts by "blooming" on MRA scans and those artifacts obscure the images and interfere with interpretation.

SUMMARY

The invention provides devices, methods, and materials for the treatment of intracranial aneurysms using a material that minimizes susceptibility artifacts in MRA images. Since images are not obscured by susceptibility artifacts associated with the aneurysm treatment device, those images are useful and reliable for evaluating the success of treatment. This allows MRA imaging to be used as a long-term follow-up tool, which aids in promptly detecting treatment stability, recanalization and/or re-bleeding and correctly determining when further treatment is required. Imaging artifacts that would be caused by materials characterized by magnetic susceptibility are avoided through the use of non-ferromagnetic materials such as metal alloys described herein. Thus, the invention provides a treatment device such as an aneurysm clip or embolization coil that includes a non-magnetic allotrope of iron or non-ferromagnetic alloy such as a non-magnetic nickel-cobalt base alloy. Preferably, the treatment device includes a 35Cobalt-35Nickel-20Chromium-10Molybdenum-Low Titanium Alloy medical grade material such as that sold under the name 35N LT by Fort Wayne Metals (Fort Wayne, Ind.) or Sandvik Bioline F562LTi sold by Sandvik Materials Technology (Sandviken, Sweden). Since the aneurysm treatment device does not cause problematic susceptibility artifacts, the success of treatment can be reliably determined by MRA imaging at follow-up. Since unneeded re-treatments are avoided while unstable, recanalized or re-bleeding aneurysm is promptly detected allowing needed re-treatment to be administered, lives are saved and outcomes are improved.

In certain aspects, the invention provides a device for the treatment of an intracranial aneurysm, the device comprising a material that is not substantially ferromagnetic. The device may be a clip or one or more embolization coils or delivery system component. The material is preferably a non-ferromagnetic metal alloy and may include one or a combination of cobalt, nickel, chromium, molybdenum and low titanium. In certain embodiments, the material is a 35Cobalt-35Nickel-20Chromium-10Molybdenum-Low Titanium alloy medical-grade material.

Aspects of the invention provide an embolization device that includes one or more coils configured for delivery into an aneurysm. The coils and/or delivery system are formed using a non-ferromagnetic alloy, which may include, for example, cobalt and titanium. Preferably, the non-ferromagnetic alloy comprises 35% cobalt, 0.5% Fe, and 34% Ni with Ti. The embolization coils may have a coiled helical or complex shape, a spiral cut geometry, or other suitable shape.

Related aspects of the invention provide a method of evaluating an aneurysm treatment. The method includes treating an aneurysm with an implantable device comprising a metal alloy that exhibits no magnetic susceptibility and subsequently imaging the aneurysm with the implantable device therein. Magnetic resonance angiography (MRA) is used to produce an image that is free of susceptibility artifacts. The MRA image is analyzed to evaluate the success of the aneurysm treatment. Preferably, the metal alloy comprises at least 30% cobalt and it may include at least 30% nickel. The metal alloy may further include iron at less than 3% with or without some amount of titanium. For example, the alloy may be substantially 35% cobalt, 0.5% Fe, 34% Ni, at least some Ti. The implantable device and/or delivery system may be an embolization coil or an aneurysm clip.

In some aspects, the invention provides a device for treating an aneurysm. The device is an aneurysm clip configured for delivery to an aneurysm, the clip comprising a non-ferromagnetic alloy. The alloy preferably includes cobalt and titanium. In some embodiments, the alloy includes about 35% cobalt, 0.5% Fe, and 34% Ni with Ti. In certain embodiments, the alloy includes at least 30% cobalt, at least 30% nickel, iron at less than 3%, and titanium.

In some embodiments, the invention includes a stent device for use with embolization coils. Such devices may include a detachment zone, release mechanism portion or delivery wire having a composition, wherein the composition has a high performance alloy that is austenitic stainless steel comprised with minimal Fe+ content and under physiological conditions, when the device is implanted into an aneurysm or vesicle, that exhibits minimal or no magnetic susceptibility or blooming artifact that may obscure visualization and subsequent interpretation. Such susceptibility artifact can be measured by overestimation factors (OEF). OEF is represented by the relation of the volume of the artifact to the volume of the coil or implant mass.

Materials of the invention are contemplated to exhibit an excellent combination of strength and corrosion resistance. Typically used in cold-worked condition, tensile strengths are comparable to 304V stainless steel. End uses in the medical field are pacing leads, stylets, catheters and orthopaedic cables. The use for guidewires and implant delivery systems is novel and new. This material is sufficiently radiopaque and non- or weakly-ferromagnetic such as to promote visualization and safety for patients undergoing MR procedures using MR systems with static magnetic field of 3.0T or less. For this discussion, the term "non-ferromagnetic" refers to metal that demonstrates extremely low ferromagnetic qualities using extremely sensitive measurements techniques (e.g., vibrating sample magnetometer, superconducting quantum interference (SQUID) magnetometer, or such). It is recognized that all metals possess some degree of magnetism, such that no metal is considered to be totally "non-ferromagnetic" in an absolute sense. Non-ferromagnetic describes the practical utility of a device as one that is non-susceptible to magnetism enough to avoid susceptibility artifacts in MRA images as shown in the examples herein.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
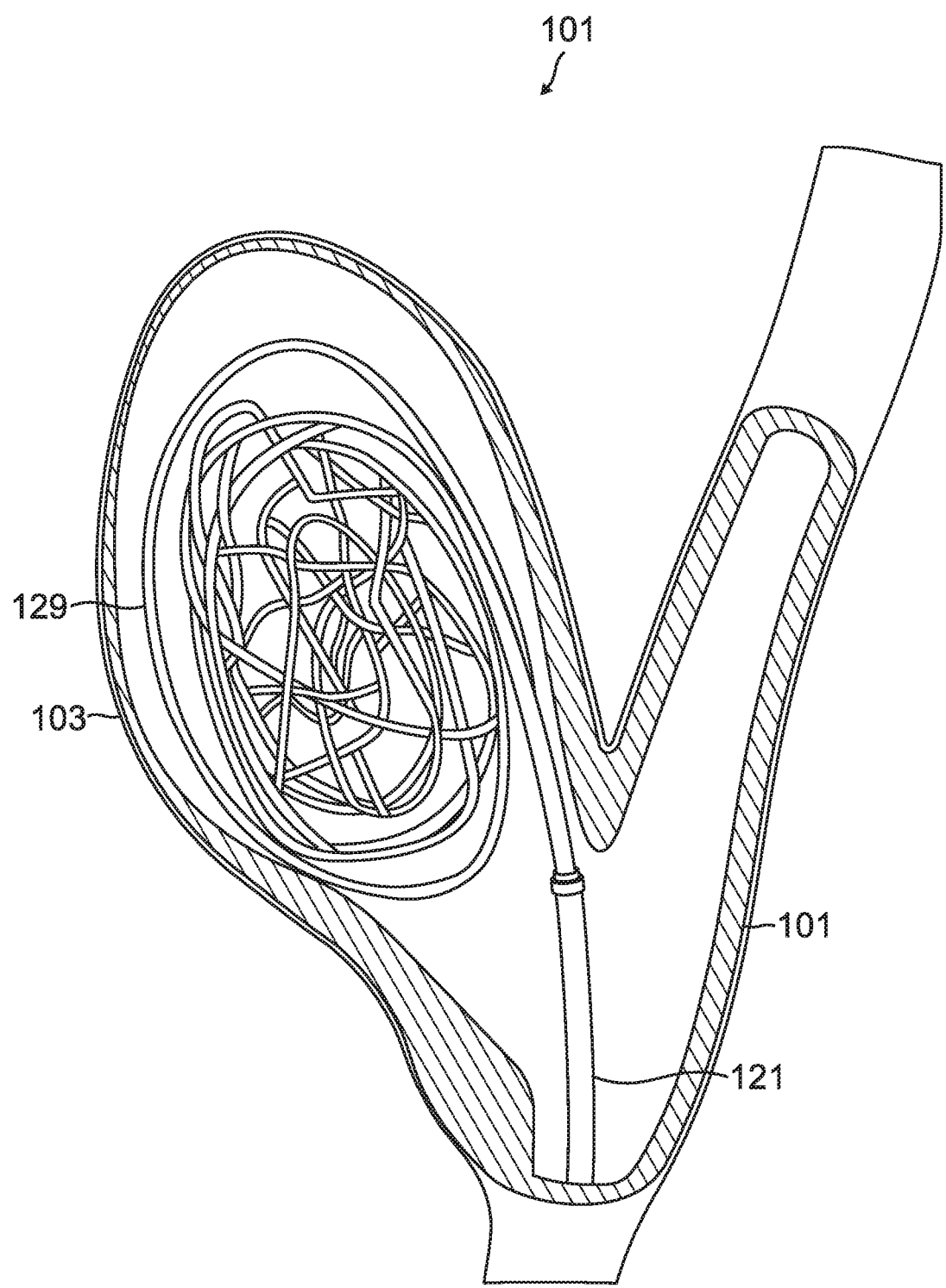
FIG. 1 illustrates an aneurysm treatment device according to certain embodiments.

The invention provides devices and methods for treatment of aneurysms that use a non-magnetic allotrope of iron or non-ferromagnetic alloy such as a non-magnetic nickel-cobalt base alloy. For example, a device may include the 35Cobalt-35Nickel-20Chromium-10Molybdenum-Low Titanium alloy medical grade material such as that sold under the name 35N LT by Fort Wayne Metals (Fort Wayne, Ind.) or Sandvik Bioline F562LTi sold by Sandvik Materials Technology (Sandviken, Sweden). Discussion of such a material may be found in Bradley et al., 2004, Optimization of Melt Chemistry and Properties of 35Cobalt-35Nickel-20Chromium-10Molybdenum Alloy Medical Grade Wire, ASM Proc Mat & Processes for Medical Devices Conference pp. 301-307.

Cerebral aneurysms occur in approximately 2% of the population. Approximately 30,000 aneurysms are treated annually in the USA. Within this therapy group, 23,000 aneurysms are embolized with coils while 7,000 are repaired endoluminally with flow diverting devices.

Aneurysms grow from a weakness in a blood vessel. Origins of aneurysms are presently unknown but linked to hypertension and injury. About 80% of aneurysms are less than 8 mm with the remainder growing to as large as 40 mm. The size and location of these aneurysms are typically diagnosed through some form of imaging such digital subtraction angiography (DSA), magnetic resonance angiography (MRA) or computed tomography (CTA). Aneurysms are typically treated by using endovascular surgical techniques to perform coil embolization. Once the abnormality is diagnosed, endovascular treatment is typically performed under DSA.

Using devices and methods of the invention, post-treatment follow-up may be performed using MRA. MRA has become increasingly popular due to its being less invasive than DSA. During MRA, contrast is infused intra-venously, which is less invasive for the patient than with DSA. MRA can also detect a degree of aneurysm occlusion and stability after coil embolization. However, it has been suspected that embolization coils due to their magnetic susceptibility produce blooming artifacts in MRA images. See e.g., Spilberg, 2011, Temporal evolution of susceptibility artifacts from coiled aneurysms on MR angiography: an in vivo canine study, AJNR Am J Neuroradiol; Walker, 2005, MR Angiographic evaluation of platinum coil packs at 1.5T and 3T: an in vitro assessment of artifact production: technical note, AJNR Am J Neuroradiol 26:848-853; Shellock, 2005, Detachable coil for cerebral aneurysms: in vitro evaluation of magnetic field interactions, heating, and artifacts at 3T, AJNR Am J Neuroradiol 26:363-366; and Kangarlu, 2000, Aneurysm clips: evaluation of magnetic field interactions with an 8.0 T MR system, J Mag Res Imaging 12:107-111. In the past, lower echo-time techniques have been employed to reduce susceptibility-induced signal intensity loss from the coil mass, thereby improving perianeurysmal visualization. If the implanted coil exhibits ferro-magnetic properties then an imaging susceptibility artifact will be created interfering with a practitioner's ability to recognize an aneurysm in-flow zone in an MRA image. The ability to visualize the abnormality treated with these devices implanted using MR/MRA/MRI offers procedural and clinical safety and benefit.

The inventors have discovered that aneurysm treatment devices that do not exhibit magnetic susceptibility provide for effective follow-up imaging via magnetic resonance angiography (MRA) since those devices do not cause artifacts on the MRA images that obscure, and thus interfere with interpretation of, portions of the images that reveal aneurysm treatment success. Non-susceptible treatment devices according to the invention may include implantable stents, embolization coils, aneurysm clips, as well as any other suitable device. In some embodiments, a non-magnetically susceptible embolization coil is provided.

FIG. 1 illustrates an aneurysm treatment device 101 according to certain embodiments. A delivery catheter 121 is used to deliver one or a set of embolization coils 129 that include a non-ferromagnetic material, preferably a non-ferromagnetic metal alloy. Catheter 121 with one or more occluding coil 129 is inserted into an artery and advanced to the abnormal blood vessel harboring the aneurysm. Once properly positioned, the coil 129 is released into position within the vessel. Coil 129 remains firmly in place by the foldability of the material. As a result of stasis, the blood will clot and form around the coil 129, completely obstructing the abnormal blood flow from the artery. Eventually a scar will form as a result of smooth muscles cells depositing at the aneurysm neck, creating a permanent seal. Coils 129 are good for fast-flowing vessels because they immediately provide stasis and stabilize the aneurysm. Coils 129 may optionally include fibers such as Dacron wool tied around the coil to aid in clot blood stasis and clot formation. In some embodiments, coil 129 is made with a non-ferromagnetic metal alloy and is visible in radiographic images.

In certain embodiments, the invention provides materials, methods, and devices for stent-assisted coil embolization.

Figure 2:
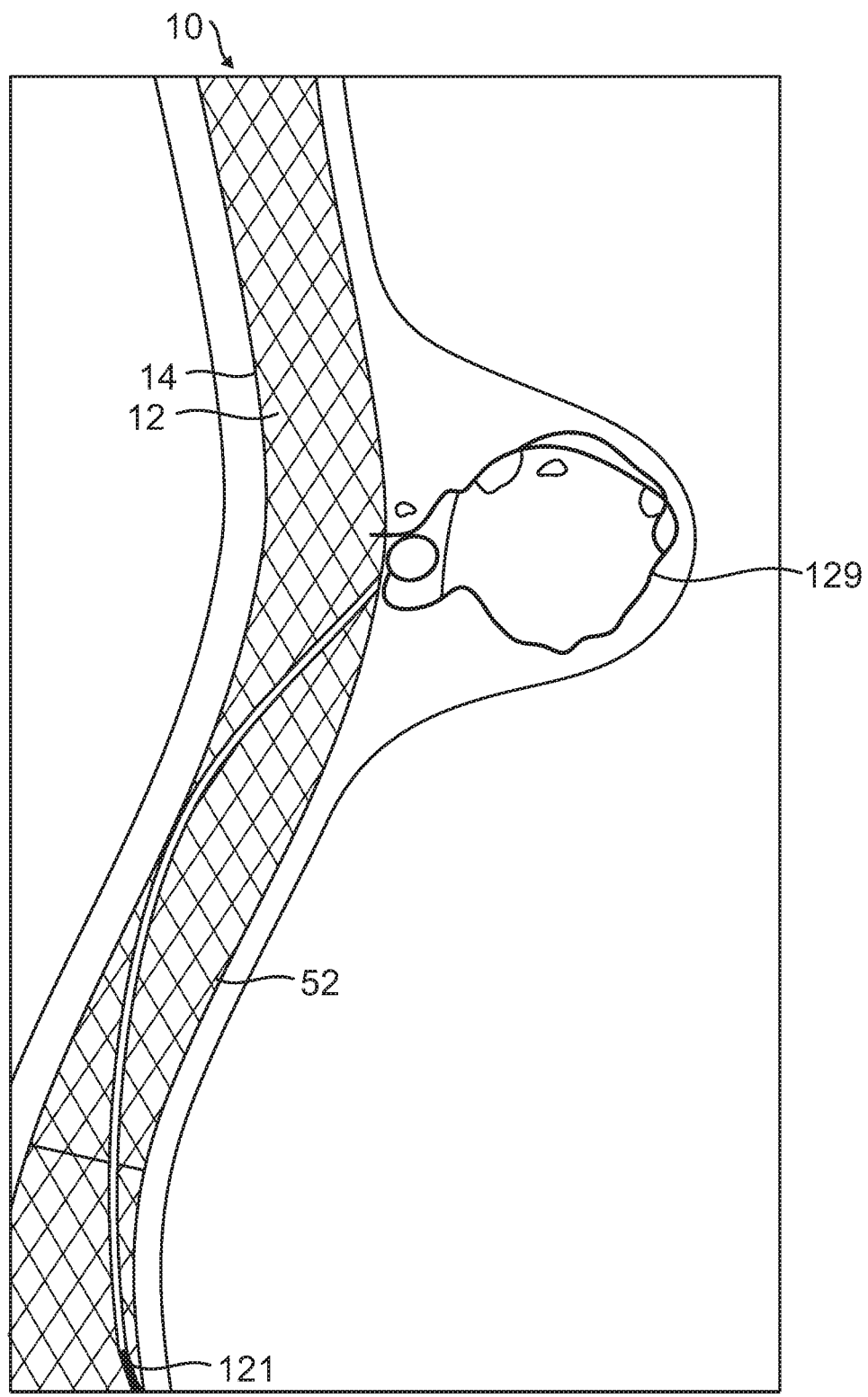
FIG. 2 depicts use of a stent device for stent-assisted coil embolization.

FIG. 2 depicts use of a stent device 10 for stent-assisted coil embolization. A stenting embolization device 10 may include a body portion made from one of the materials discussed herein, a metal, or a metal alloy known in the art of stent-assisted coil embolization. For example, contemplated body portions may comprise stainless steel, titanium, nitinol, etc. The stent diameter is typically between 1.5 and 6.0 mm, the stent wall thickness is typically between 30 and 100 microns and the stent surface is coated via vapor deposition with a thin 5 to 30 micron layer of tantalum.

Stent device 10 as shown includes multi-sided cells 52 that allow micro-catheters 121 to extend through a wall of the stent device 10. Stent device 10 is formed of a material in a suitable shape such as a mesh or a network of strut-like elements that define open cells 52. The material of stent device 10 may have a surface 12 that is coated with a tantalum coating 14.

Figure 3:
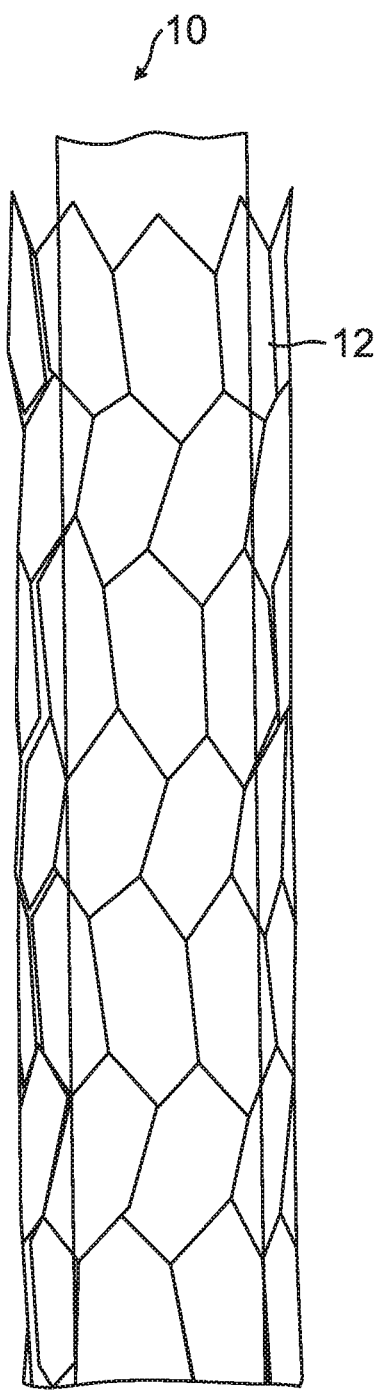
FIG. 3 shows embolization device having an open cells.

FIG. 3 shows embolization device 10 having an open cells 52. The construction details shown in FIG. 3 may be provided by forming the body of stent device 10 of a non-ferromagnetic material, nitinol, or any other suitable material such as stainless steel, tungsten, cobalt-chromium, and the like. As noted before, the various components of the embolization device 10 can be made of different materials. In some embodiments, stent device 10 includes a non-ferromagnetic alloy. Stent device 10 may use or include an alloy that includes cobalt and titanium. The material referred to as 35N LT may be used for stent device 10 and the material preferably includes 35% cobalt, 0.5% Fe, and 34% Ni with Ti.

Figure 4:
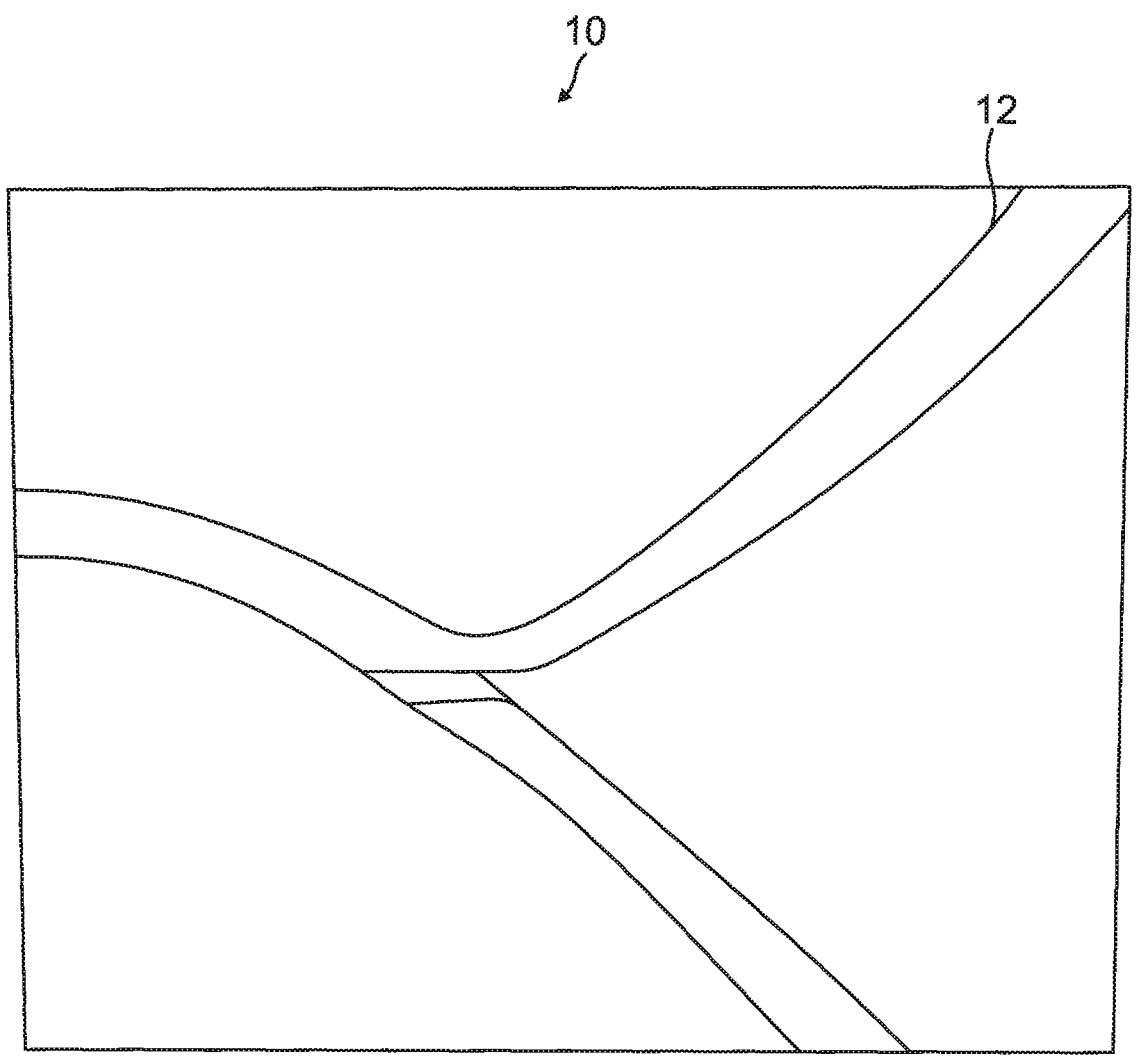
FIG. 4 gives a close-up view of the mesh or strut-like elements of a stent device.

FIG. 4 gives a close-up view of the mesh or strut-like elements of stent device 10 that define open cells 52. The material of stent device 10 presents a surface, which may optionally be provided with a tantalum coating 14. As shown in FIG. 4, the multi-sided cells 52 are sufficiently wide to allow passage of guidewires or micro-catheters such as about 1 to 3 mm.

As mentioned above, in certain embodiments, a device of the invention includes a surface with a tantalum coating 14.

Figure 5:
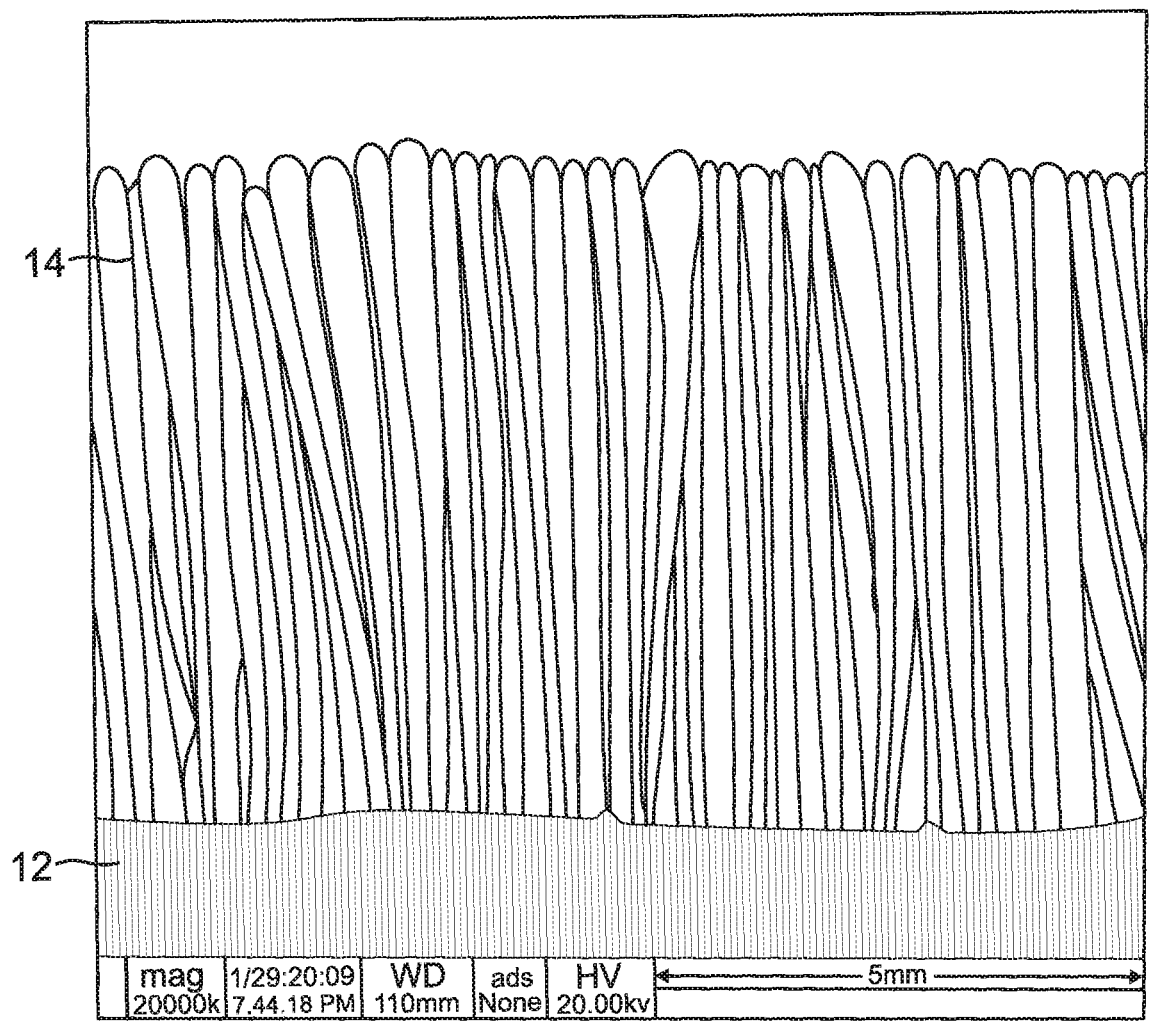
FIG. 5 gives an electron micrograph cross section of a tantalum layer.

FIG. 5 gives an electron micrograph cross section of an exemplary embolization device with a tantalum layer 14 coated onto surface 12 of stent device 10. The depicted tantalum coating 14 is an optional embodiment that may be included with other devices discussed herein and may be created by, for example, vapor-deposition methods such as carbon vapor deposition or plasma vapor deposition.

Figure 6:
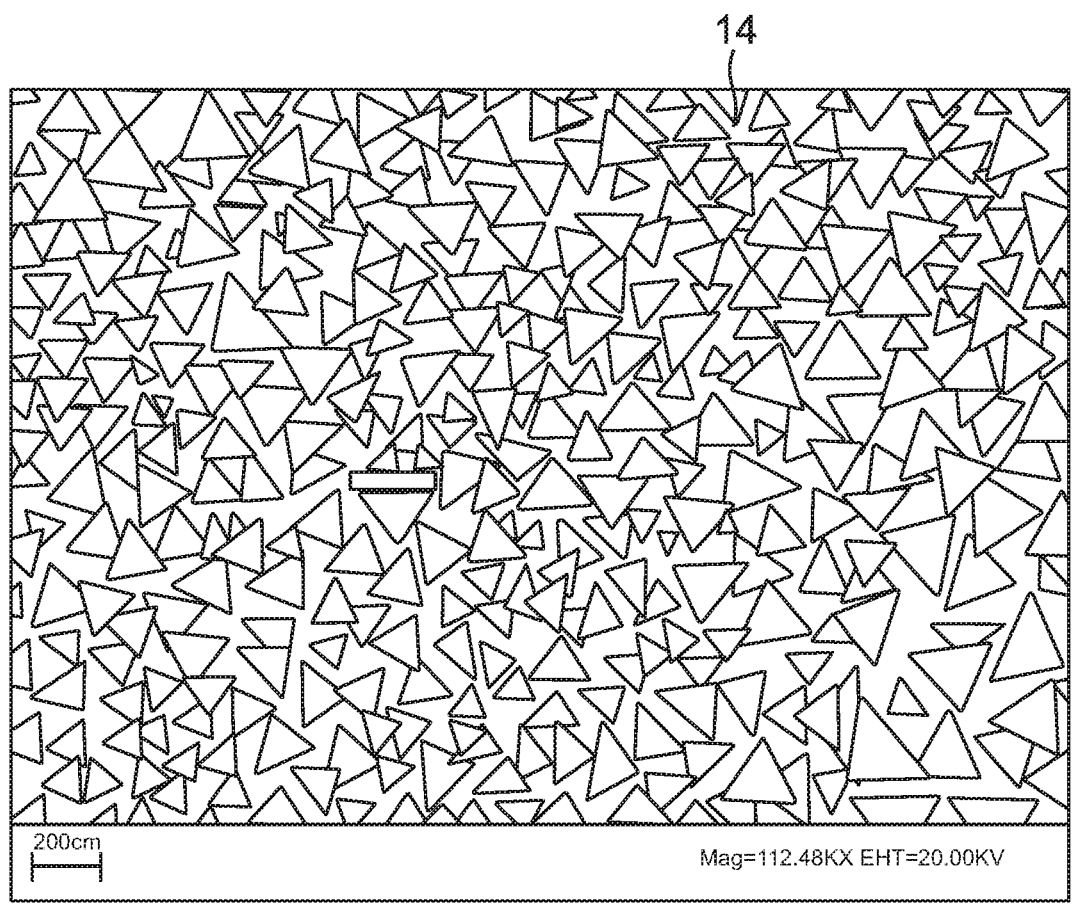
FIG. 6 is an electron micrograph in top view of a tantalum layer.

FIG. 6 is an electron micrograph in top view of an exemplary embolization device with a tantalum layer 14 coated onto surface 12 of stent device 10. The optional tantalum coating 14 is coupled to the surface 12 of a device of the invention. With reference back to FIGS. 3 & 4, the embolization device surface 12 has sufficient width and surface area to receive a tantalum coating 14 when device diameter is 1.5 to 6.0 mm and length is 1 cm to 5 cm. The tantalum coating 14 is radiopaque and positively charged to be visualized the entire length and attract and interacts electrostatically with negatively charged bodily fluids such as cells, blood, elements such as oxygen or tissue to the embolization device surface 12 creating a stable placement to maintain embolization device location and position. Of course, it should be noted that the radiopaque electronegative metal need not provide an immediate positive charge, but may be initially present as a metallic electrically neutral metal.

Upon contact with electrolyte, body fluid, or tissue, a redox reaction may occur (or may be induced) that converts the electrically neutral material into a positively charged surface. Such redox reaction may be entirely due to the chemical components present in the body fluid or tissue, or may be induced by added chemicals or during an external (pre-implantation) redox process. Thus, it should be noted that the electropositive surface might be in truly ionic form, or present as a metal oxide (e.g., tantalum pentoxide) that acts as an intermediate conductor. Alternatively, and especially where the metal is converted to a metal oxide, it should be noted that the binding interaction between the metal oxide and the tissue/body fluid may also be due to hydrogen bonds, hydrophilic interaction, and even via apatite-type reaction.

While not wishing to be bound by any particular theory or hypothesis, the inventors contemplate that the most common type of ionic bonding is seen in compounds of metals and nonmetals. Certain metals, such as tantalum, are characterized by having a small number of electrons in excess of a stable, closed-shell electronic configuration. As such, they have the tendency to lose these extra electrons in order to attain a stable configuration. This property is known as electro-positivity. Many non-metals, on the other hand, are characterized by having an electron configuration just a few electrons short of a stable configuration. As such, they have the tendency to gain more electrons in order to achieve a stable configuration. This tendency is known as electronegativity. When a highly electropositive metal such as tantalum is combined with a highly electronegative nonmetal, such as bodily tissue and fluids, the extra electrons from the metal, tantalum, atoms are transferred to the electron-deficient nonmetal atoms in the bodily tissue or fluid. This reaction produces metal cations and nonmetal anions, which are attracted to each other to form an ionic compound.

While discussed herein and above in terms of coil embolization, aspects and embodiments of the invention provide aneurysm clips made of a non-ferromagnetic material that are not magnetically susceptible and thus do not exhibit susceptibility artifacts in images captured using magnetic resonance such as MRA images. During microsurgical clipping, a small clip is used to stop blood flow into the aneurysm. The clip is placed on the neck (opening) of the aneurysm to obstruct the flow of blood, and remains inside the brain. The invention provides an aneurysm clip formed with a non-ferromagnetic alloy that includes cobalt and titanium and that preferably includes no copper.

Figure 7:
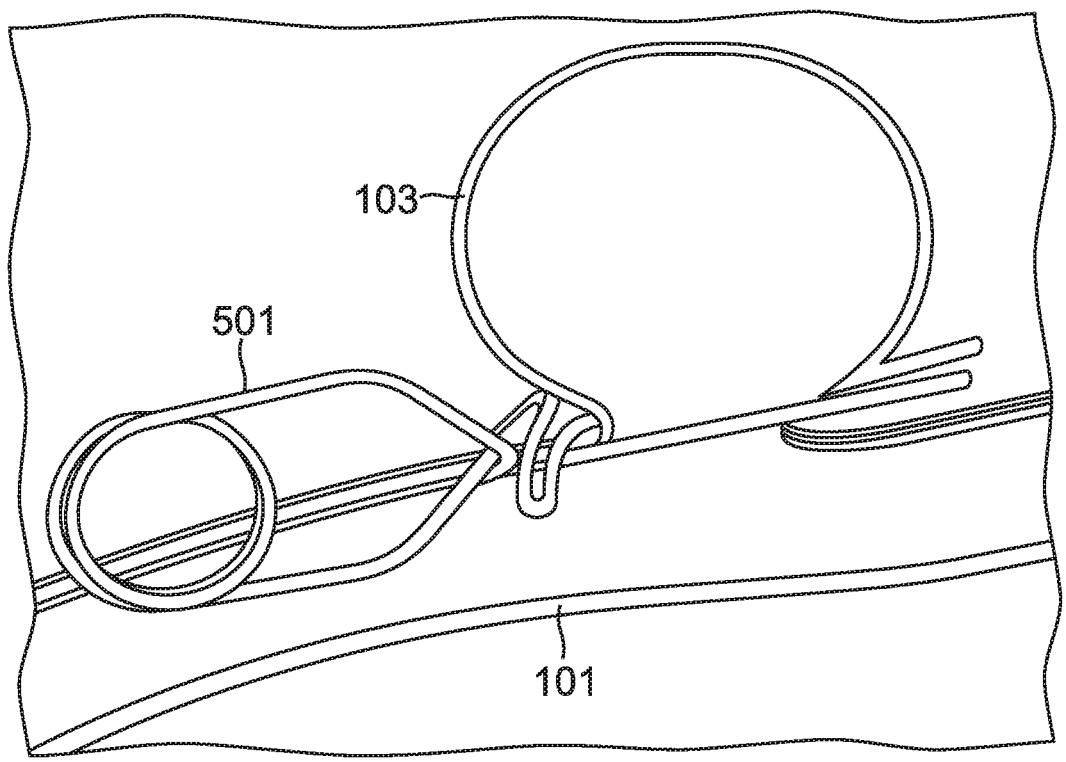
FIG. 7 shows a non-ferromagnetic aneurysm clip.

FIG. 7 shows a non-ferromagnetic aneurysm clip 501 being used to treat aneurysm 103 on a blood vessel 101. Clip 501 includes a non-ferromagnetic alloy. In a preferred embodiment, devices of the invention use an alloy that includes cobalt and titanium such as the material referred to as 35N LT. The material preferably includes 35% cobalt, 0.5% Fe, and 34% Ni with Ti. Table 1 shows material composition according to certain embodiments.

Additionally or alternatively, a device of the invention may include, for any given part or component, a material such as nitinol, (or any other suitable material, including stainless steel, tungsten, cobalt-chromium, etc.). Further, the various components of the embolization device 10 can be made of different materials.

The advantages of the present inventive subject matter include, without limitation, that the devices contemplated herein do not create susceptibility artifacts in magnetic resonance imaging.

TABLE 1

Material composition comparison

| | 35N LT alloy | 316LVM Stainless steel | 304V Stainless Steel |
|---|---|---|---|
| | | FWM Avg. Wt. % | |
| Carbon | 0.010 | 0.023 | 0.073 |
| Manganese | 0.06 | 1.84 | 1.310 |
| Silicon | 0.03 | 0.37 | 0.700 |
| Phosphorus | 0.002 | 0.014 | 0.021 |
| Sulphur | 0.001 | 0.001 | 0.030 |
| Chromium | 20.58 | 17.57 | 18.58 |
| Nickel | 34.82 | 14.68 | 8.65 |
| Molybdenum | 9.51 | 2.79 | 0.16 |
| Cobalt | Balance | | 0.10 |
| Copper | | 0.03 | 0.17 |
| Nitrogen | | 0.03 | 0.034 |
| Titanium | <=0.01 | | |
| Iron | 0.52 | Balance | Balance |
| Boron | 0.010 | | |

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc. All patents, published patent applications, and non-patent literature mentioned herein are incorporated by reference in their entirety for all purposes.

EXAMPLES

Example 1: Coil of Non-Ferromagnetic Alloy Such as 35N LT has Susceptibility Artifact with OEF <50% OEF for Ferromagnetic Coil(s)

Endovascular procedures for the treatment of intracranial aneurysms and long-term imaging follow-up to assess need for retreatment are discussed. See Raymond et al., 2003, Long-term angiographic recurrences after selective endovascular treatment of aneurysms with detachable coils, Stroke 34(6):1398-403; and Molyneux et al., 2005, International subarachnoid aneurysm trial (ISAT) of neurosurgical clipping versus endovascular coiling in 2143 patients with ruptured intracranial aneurysms: a randomised comparison of effects on survival, dependency, seizures, rebleeding, subgroups, and aneurysm occlusion, Lancet 366(9488):809-17. Due to high resolution, sensitivity to flow and non-invasive nature, 3D-time of flight (3D-TOF) magnetic resonance angiography (MRA) and contrast-enhanced (CE) MRA provide excellent characterization of the cerebral vasculature and aneurysms. See Anzalone et al., 2000, Three dimensional time-of-flight MR angiography in the evaluation of intracranial aneurysms treated with Guglielmi detachable coils. AJNR Am J Neuroradiol 2000; 21(4):746-52; Boulin & Pierot L., 2001, Follow-up of intracranial aneurysms treated with detachable coils: comparison of gadolinium-enhanced 3D time-of-flight MR angiography and digital subtraction angiography, Radiology 219(1):108-13; and Nome et al., 2002, MR angiography in the follow-up of coiled cerebral aneurysms after treatment with Guglielmi detachable coils, Acta Radiol 43(1):10-4. MRA is a promising imaging modality for long term follow up to evaluate aneurysm residual patency or recanalization as well as parent vessel abnormalities. Magnetic susceptibility or blooming artifact that may obscure visualization and subsequent interpretation is addressed. See Gonner et al., 1998, MR angiography with ultrashort echo time in cerebral aneurysms treated with Guglielmi detachable coils, AJNR Am J Neuroradiol 19(7):1324-8; and Schmalbrock et al., 1990, Volume MR angiography: methods to achieve very short echo times. Radiology 175(3):861-5.

Materials and Methods

Anesthesia, Analgesia and Antibiotic Regimens

All animal experiments were performed in accordance with a protocol approved by our Institutional Animal Care and Use Committee. All procedures were performed under general anesthesia and using strict aseptic technique. Prior to all surgical or imaging procedures, the animals were pre-anesthetized by an intramuscular injection of acepromazine (0.06 mg/kg) and glycopyrrolate (0.01 mg/kg). Anesthesia was induced by an intravenous injection of thiopental (15 mg/kg) or propofol (3 mg/kg) and maintained with mechanical ventilation of 1-4% isoflurane. The physiologic status of the animal was assessed using continuous monitoring of respiration rate, heart rate, oxygen saturation level, end-tidal CO2 level and temperature.

Prior to surgical procedures, the animals were given buprenorphine (0.02 mg/kg, IM, 1×) and a fentanyl patch was applied (75 mcg/hr, transdermal, 3 days). During the surgical intervention, Cefazolin (20 mg/kg, IV) is administered and repeated every two hours until closure for prophylactic infection control.

Aneurysm Creation

One mongrel canine (sex: female, weight: 22 kg) was used to investigate the aims of the study. The details of the venous pouch surgical aneurysms construction have been available for decades and is described elsewhere. See German W, Black S. Experimental production of carotid aneurysms. New Engl J Med 1954; 250:104-06. Briefly, two venous side-wall aneurysms were created on each common carotid artery (CCAs) for a total of four aneurysms. Two arteriotomies were made in each common carotid artery, followed by an end-to-side anastomosis of a resected portion of the external jugular vein to the arteriotomy site. The top of the vein pouch was ligated at a linear distance of between 4-6 mm from the parent artery.

Interventional Procedure

After allowing the aneurysms to heal for a period of 3 weeks, the animal was prepared for the coiling procedure. The right inguinal region of the animal was prepared for a femoral cutdown followed by placement of a 6 Fr hemostatic introducer in the left femoral artery using a modified Seldinger technique. The introducer was secured in place with the distal aspect of the femoral artery ligated. Baseline activated clotting time (ACT) was measured and a loading dose of heparin (75 IU/kg) was administered intravenously to maintain ACT levels above approximately twice that recorded at baseline. A 6 Fr guide catheter was placed through the introducer and navigated past the origin of the common carotid artery in preparation for precoiling 3D and planar angiography. Measurements were taken to characterize the implant sites based on the dimensions of the aneurysm and the parent vessel diameter. At this point it was determined that three of the four aneurysms had thrombosed and could not be used. Due to the fact that there was only one available aneurysm, it was decided that the maxillary artery would be occluded in order to serve as the second site for coiling. Additionally, the viable aneurysm was chosen for embolization with the 35N LT delivery pusher and platinum coils while the 304 V delivery pusher and platinum coils would be used in the vessel occlusion site.

A 2 tipped SL-10 microcatheter was advanced into the aneurysm in preparation for coil embolization. Coils were deployed and detached in accordance with the representative Directions for Use (DFU) for each coil. Verification of coil alignment relative to the microcatheter, confirmation of coil detachment and assessment of the condition of the aneurysm were obtained using angiography throughout the procedure. The left distal aneurysm was embolized with the Barricade 35N TL delivery pusher and platinum coils, while the right maxillary artery was occluded with the 304V delivery pusher and platinum coils.

MR Imaging

Following completion of the aneurysm coiling, the animals were transferred to the 3T MRI (Achieva 3.0T, Philips Healthcare, Best, The Netherlands) for imaging. Anesthesia was maintained with isoflurane for the MRI procedure. MR imaging was performed on animals in ventral recumbency head first into the magnet. The neck of the animal was placed into a Philips SENSE (phased array) 8-element, receive-only knee coil. Fast scout images were taken with the full array of coils turned on. The built-in quadrature body coil was used for radiofrequency transmission. The MRI technique included coronal T1 unenhanced turbo spin echo, axial 3D TOF MRA, phase contrast MRA, and coronal CE-MRA sequences (Table 2). The animal was returned to the MRI center at one and four weeks after coil embolization for repeat imaging studies as previously performed (Table 2). In-plane resolution on angiography sequences was approximately 0.4 mm and slice thickness 0.7 mm. Gd-DTPA (0.1 mmol/kg, IV) was administered prior to CE-MRA with bolus tracking; namely, the sequence was commenced upon visualization of contrast entering the ascending aorta. Total MR imaging time was approximately 45 minutes. The animal was returned for repeated MR study one, and four weeks post-embolization using the same protocol. Table E1 gives MRI acquisition parameters.

TABLE E1

MRI acquisition parameters; TR: repetition time, TE: echo time, FA: flip angle, NSA: number of signal averages, Acq matrix: acquisition matrix, FOV: field of view; T1W-TSE; T1 weighted turbo spin echo; TOF: time of flight; PC-MRA: phase contrast MRA; CE-MRA: contrast enhance MRA.

| | TR (ms) | TE (ms) | FA (°) | NSA | Scan Time (min) | Slices | Slice thickness (mm) | Gap (mm) | Acq matrix | FOV (mm) |
|---|---|---|---|---|---|---|---|---|---|---|
| Sequence 1 (T1W-TSE) | 661 | 9.2 | 90 | 1 | 3:09 | 39 | 3 | 0 | 384 × 384 | 175 |
| Sequence 2 (TOF, 3.5TE) | 25 | 3.5 | 20 | 1 | 4:37 | 114 | 1.4 | −.7 | 384 × 386 | 150 |
| Sequence 3 (TOF, 5TE) | 25 | 5.0 | 20 | 1 | 4:37 | 114 | 1.4 | −.07 | 384 × 386 | 150 |
| Sequence 4 (TOF, 6.9TE) | 30 | 6.9 | 20 | 1 | 5:17 | 80 | 2 | −1.0 | 384 × 386 | 150 |
| Sequence 5 (PC-MRA) | 18 | 4.7 | 12 | 1 | 5:24 | 50 | 2.0 | −1.0 | 384 × 386 | 150 |
| Sequence 6 (CE-MRA) | 5.6 | 1.6 | 25 | 1 | 0:44 | 100 | 1.4 | −0.7 | 376 × 167 | 150 |

Quantitative Analysis-OEF Methodology The aneurysm and the coil mass volumes were calculated using the formula:

$$V = \tfrac{1}{6}\pi h d^2$$

where h is the height of the aneurysm defined as the perpendicular bisector of the line that forms the neck of the aneurysm that extends to the most ventral aspect of the aneurysm. The aneurysm diameter (d) is the distance normal to the line forming the height at the widest part of the aneurysm Additionally, the volumes of the native aneurysm and the coil mass were estimated using 3D angiography as previously detailed. See Piotin et al., 2006, Ellipsoid Approximation versus 3D Rotational Angiography in the Volumetric Assessment of Intracranial Aneurysms, AJNR Am J Neuroradiol 27:839-42.

The volume of coils was calculated by assuming that the coil is a solid cylinder, namely the cross section area was multiplied by the coil length and summed for all coils implanted. From these measurements, the packing density was calculated by dividing the volume of coils by the native aneurysm volume. See Wakhloo et al., 2007, Complex-shaped platinum coils for brain aneurysms: higher packing density, improved biomechanical stability, and midterm angiographic outcome, AJNR Am J Neuroradiol 28(7):1395-400. Some error is observed in these calculations since the vein pouch is very elastic and can stretch as the coils are implanted. Also, the parent vessel diameters were measured both proximally and distally to the aneurysm as well as at the narrowest segment of the implant site.

The MRA sequences were exported to a DICOM file and analyzed using a Dell T7400 workstation with dual quad core Intel Xenon processors, 12 Gb RDIMM memory, and dual NVIDIA graphic cards. Each sequence was imported into Mimics 15.1 (Materialise, Leuven, Belgium) for 3D reconstruction and volume analysis. Manual regions of interest (ROIs) were drawn that encompass the area of susceptibility artifact. This manual segmentation was used to limit subsequent thresholding thereby ensuring small vessels close to the artifact were not incorporated into the artifact volume measurements. Manually segmented ROIs were thresholded to a value of 70% of the mean signal from a neighborhood close to the artifact (ASTM F2119)—any pixel less than this value was said to be part of the artifact caused by the coils. These areas were then reconstructed into 3D volumes and their volume was measured in cubic millimeters.

The overestimation factor was calculated from this volume:

$$OEF = v(\text{Artifact})/v(\text{Coil Mass})$$

See Walker et al., 2005, MR angiographic evaluation of platinum coil packs at 1.5T and 3T: an in vitro assessment of artifact production: technical note, AJNR Am J Neuoradiol 26(4):848-53. At every time point, a second set of 3D rotational CT images was acquired to allow for the coil mass to be re-measured to check for coil compaction. It was found that the coils had compacted a slight amount (9%).

All acquired data are compared to previously obtained results available in the peer-reviewed literature. See Spilberg et al., 2012, Temporal Evolution of Susceptibility Artifact from Coiled Aneurysms on MR Angiography: An In Vivo Canine Study, AJNR Am J Neuroradiol 33:655-60.

Results

One aneurysm and one vessel occlusion were embolized with the coils delineated in the Table E2.

TABLE 2

List of all coils used in the study. All coils are listed by secondary shape diameter (mm) × coil length (cm).

| Location<br>Coil Type | Left CCA aneurysm<br>35NLT and platinum | Right Maxillary Artery<br>304V and platinum |
|---|---|---|
| Coil 1 | 8 × 21 | 4 × 8 |
| Coil 2 | 7 × 19 | 5 × 13 |
| Coil 3 | 4 × 13 | 4 × 8 |
| Coil 4 | 7 × 19 | 3 × 6 |
| Coil 5 | 3 × 10 | 2.5 × 4 |
| Coil 6 | 3 × 10 | 3 × 6 |
| Coil 7 | 4 × 13 | 2 × 2 |
| Coil 8 | 2.5 × 4 | 2.5 × 4 |
| Coil 9 | 2.5 × 4 | 2 × 2 |

TABLE 2-continued

List of all coils used in the study. All coils are listed by secondary shape diameter (mm) × coil length (cm).

| Coil 10 | 2 × 2 |
| Coil 11 | 2 × 2 |

Quantitative Analysis

The volume of the aneurysm, volume of the coil mass, volume of coils and packing density are reported in Table E3. Additionally, the parent vessel dimensions were recorded and are available in Table E4.

TABLE E3

Volumes and packing densities

| Aneurysm Location | Left | Right |
|---|---|---|
| Coil Type | 35N LT and platinum | 304V and platinum |
| Aneurysm Volume (mm3) | 277 | 53.5 |
| Coil Volume (mm3) | 72.4 | 29.8 |
| Packing Density (%) | 0.26 | 0.56 |
| Neck size (mm) | 3.85 | 2.27 |
| Coil Mass Volume (mm3) | 317 | 116 |

Artifact volume, and overestimation factors (Equation 2) for MRI studies performed immediately post-implantation, and at one-week, and four-weeks were calculated. FIGS. 1-3 (OEF) show the average of each method by coil type at each given time point. Due to the small number of samples in this test, no statistical analysis was performed. Notably, sequence 1 was used for orientation and positioning of later MR sequences and therefore was not designated to be analyzed. CE-MRA, sequence 6, could not be evaluated for the OEF of the right maxillary artery coil mass due to sequence parameters that could not create an image appropriate for identification of the coil mass artifact with relation to the surrounding sinuses.

TABLE E4

Size of parent vessel proximal and distal to embolization site (mm). The minimum diameter of the parent vessel along the neck of the aneurysm is also provided (central).

| Aneurysm Location | Proximal (mm) | Central (mm) | Distal (mm) |
|---|---|---|---|
| Left | 3.71 | 3.65 | 3.53 |
| Right | 2.71 | 2.55 | 1.28 |

Figure 8:
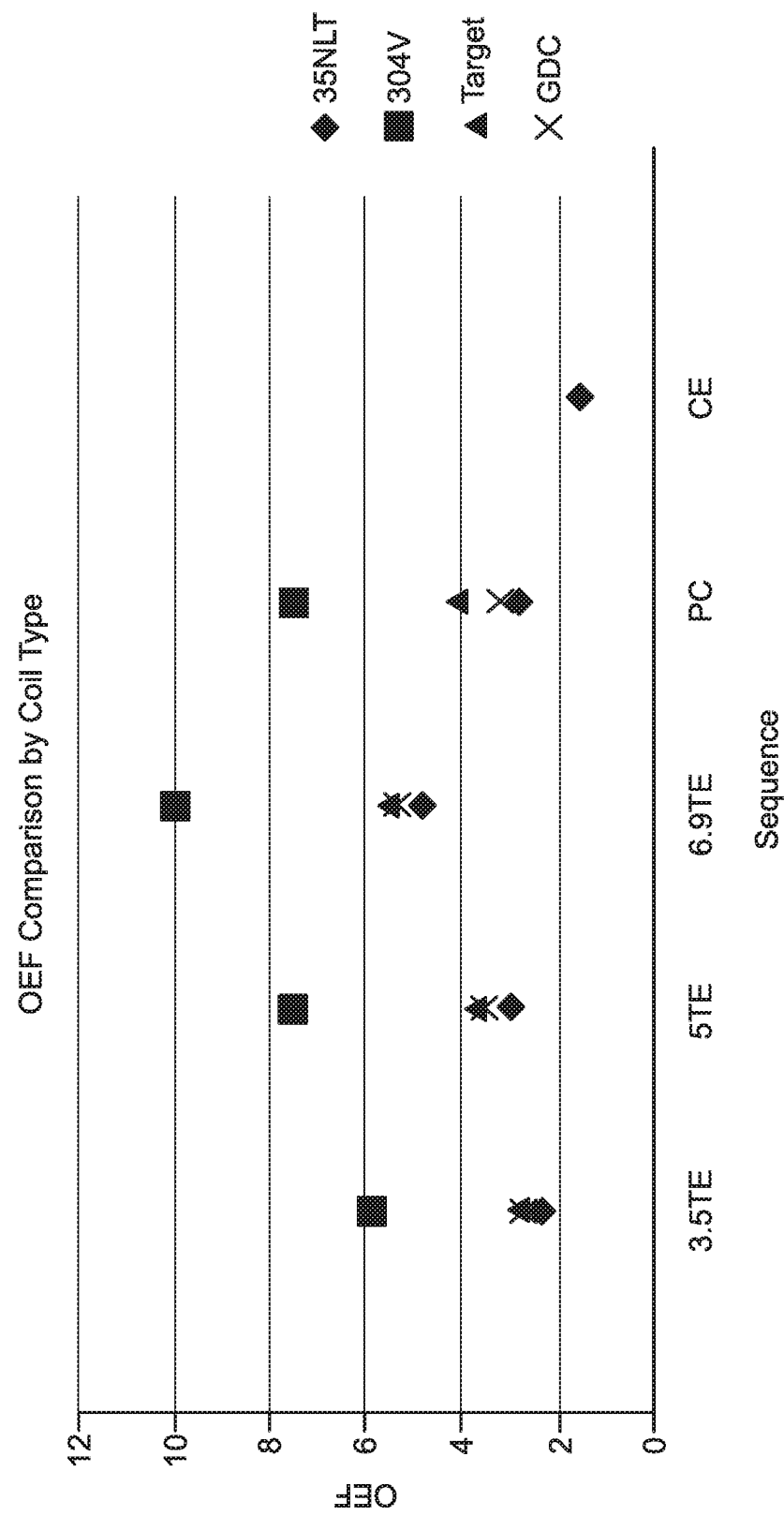
FIG. 8 shows post-procedural average over-estimation factors (OEFs).

FIG. 8 shows post-procedural average OEFs (n=6 for Target 316LVM, n=5 for GDC 10, n=1 for 304V, n=1 for 35N LT). FIG. 8 reveals an OEF for 304V of 10 and an OEF for 35N LT of about 4.7 on the 6.9TE sequence.

Figure 9:
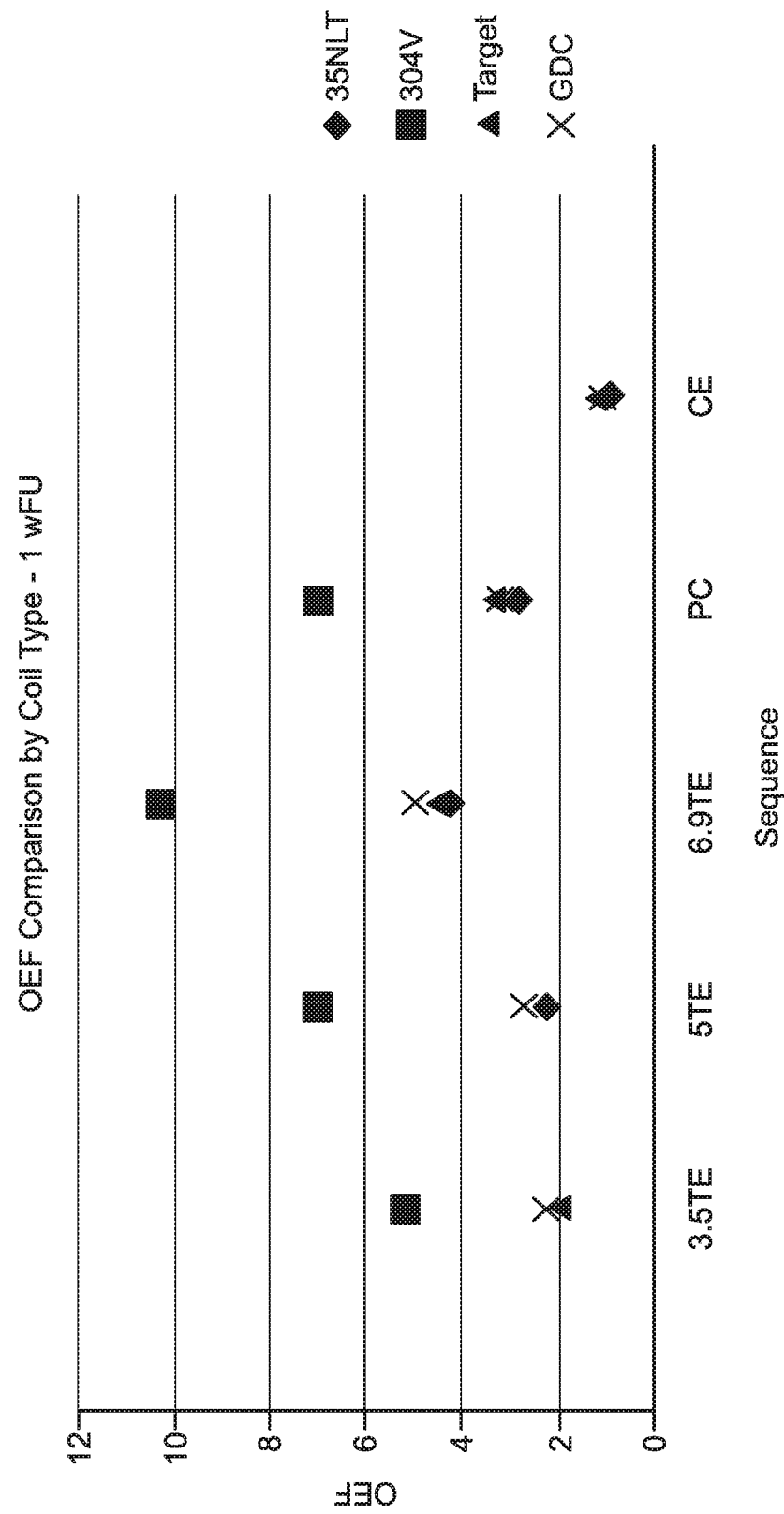
FIG. 9 gives OEF results from a one-week follow-up MR.

FIG. 9 gives results from a one-week follow-up MR: average OEFs (n=6 for Target 316LVM, n=5 for GDC 10, n=1 for 304V, n=1 for 35N LT).

Figure 10:
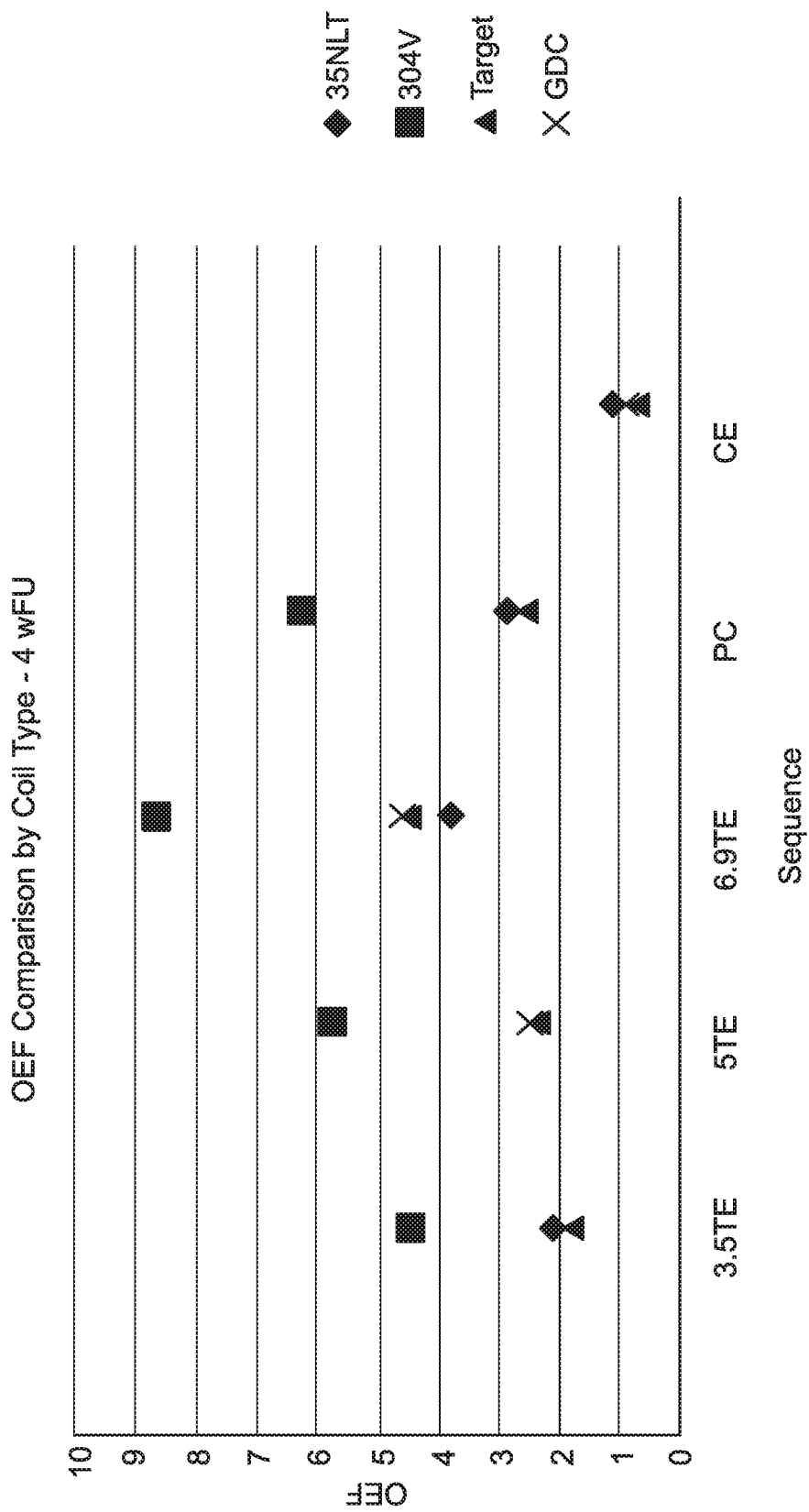
FIG. 10 gives a four-week follow-up MR.

FIG. 10 gives a four-week follow-up MR: OEFs (n=6 for Target 316LVM, n=5 for GDC 10, n=1 for 304V, n=1 for 35N LT). In the 6.9 TE sequence, for example, the OEF for the cobalt nickel alloy is less than 4 and the OEF for 304V is just under 9. Thus materials of the invention can provide an OEF of about 50% of the OEF of a prior-art material. The 35N LT material may decrease susceptibility artifacts by half as measured by OEF.

Figures 11, 12:
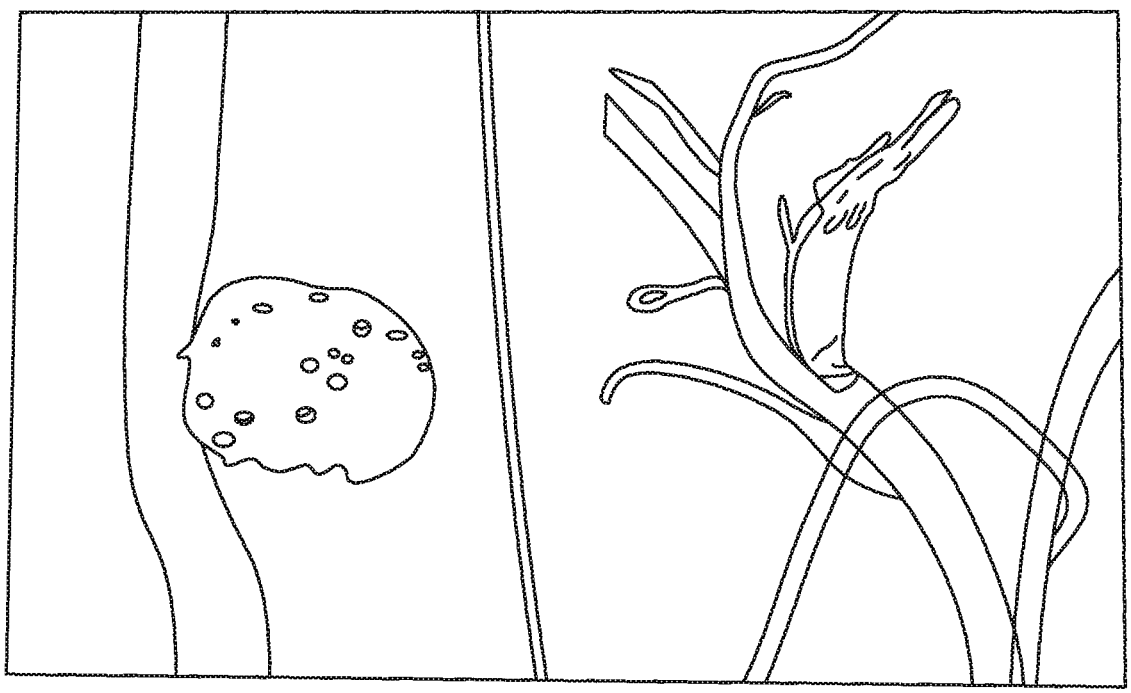
FIG. 11 shows a DSA image of a left aneurysm.
FIG. 12 shows a DSA image of the right vessel occlusion.

FIG. 11 shows a DSA image of the left aneurysm.

FIG. 12 shows a DSA image of the right vessel occlusion.

Figures 13, 14:
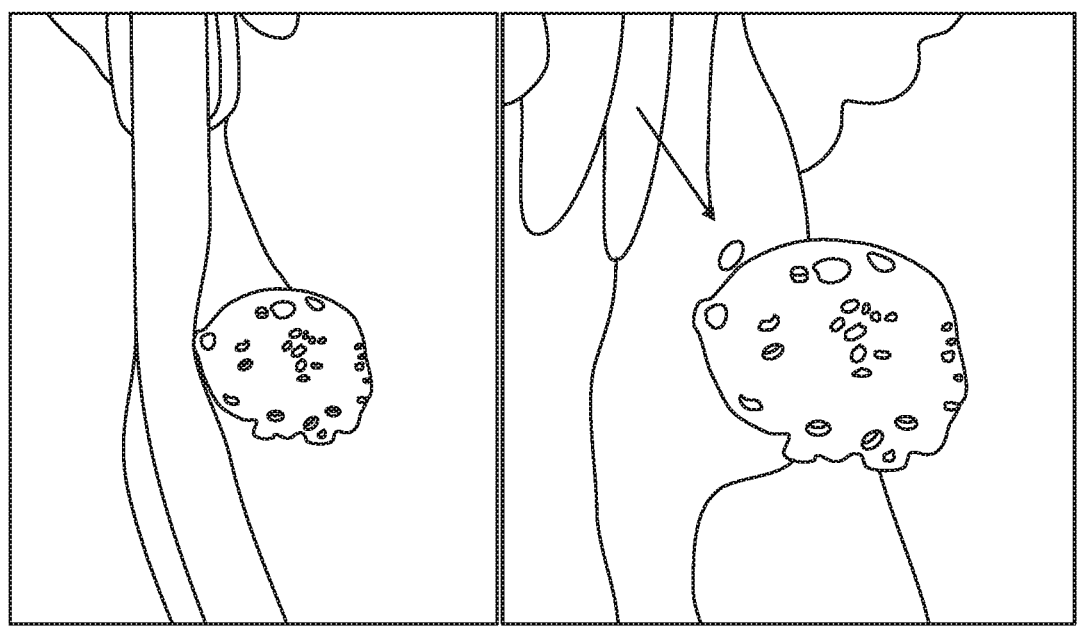
FIG. 13 shows a four-week follow up DSA, artery phase.
FIG. 14 shows a four-week follow up DSA, venous phase.

FIG. 13 shows a four-week follow up DSA, artery phase.

FIG. 14 shows a four-week follow up DSA, venous phase, arrow points to small neck remnant that is visible.

Figure 15:
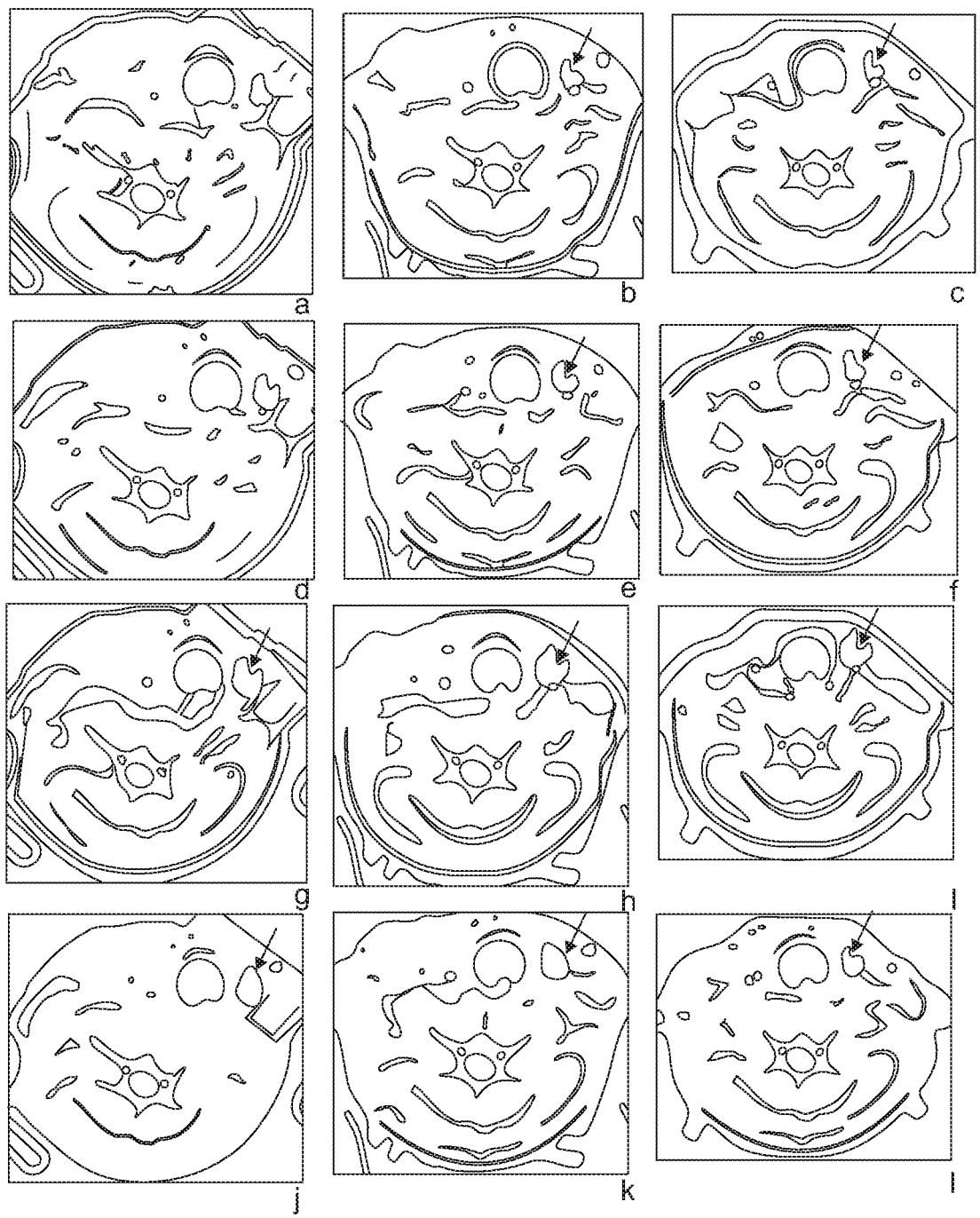
FIG. 15 presents a series of axial MRI images.

FIG. 15 presents a series of axial MRI images. The arrows point to left CCA aneurysm artifact. a) post implant 3.5 ms TE b) 1wFU 3.5 ms TE c) 4wFU 3.5 ms TE d) post implant 5 ms TE e) 1wFU 5 ms TE f) 4wFU 5 ms TE g) post implant 6.9 ms TE h) 1wFU 6.9 ms TE i) 4wFU 6.9 ms TE j) post implant PC k) 1wFU PC l) 4wFU PC a) b) c) d) e) f) g) h) i) j) k) l)

Figure 16:
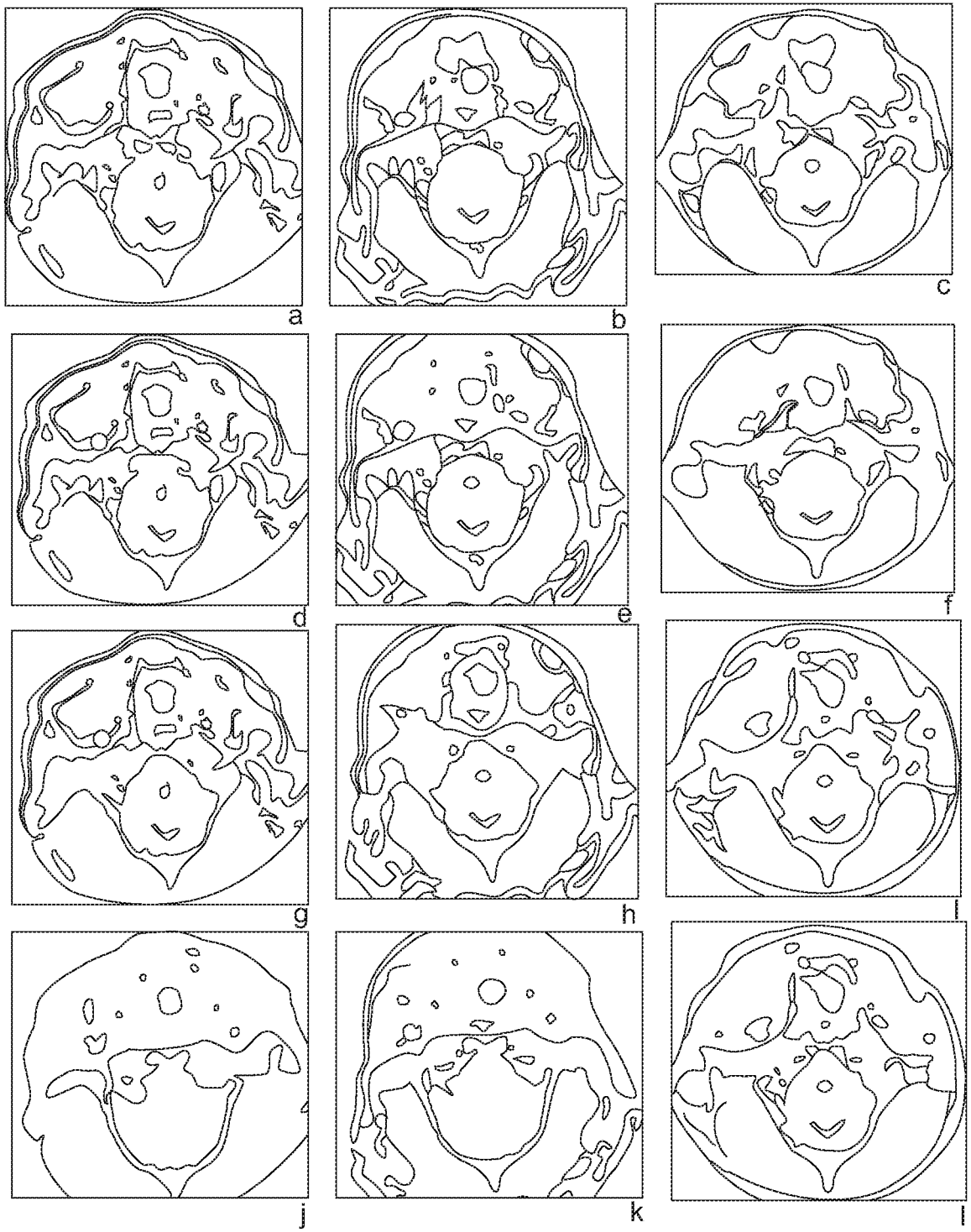
FIG. 16 presents a series of axial MRI images.

FIG. 16 presents a series of axial MRI images. The arrows point to right maxillary artery occlusion artifact, a) post implant 3.5 ms TE b) 1wFU 3.5 ms TE c) 4wFU 3.5 ms TE d) post implant 5 ms TE e) 1wFU 5 ms TE f) 4wFU 5 ms TE g) post implant 6.9 ms TE h) 1wFU 6.9 ms TE i) 4wFU 6.9 ms TE j) post implant PC k) 1wFU PC.

Figure 17:
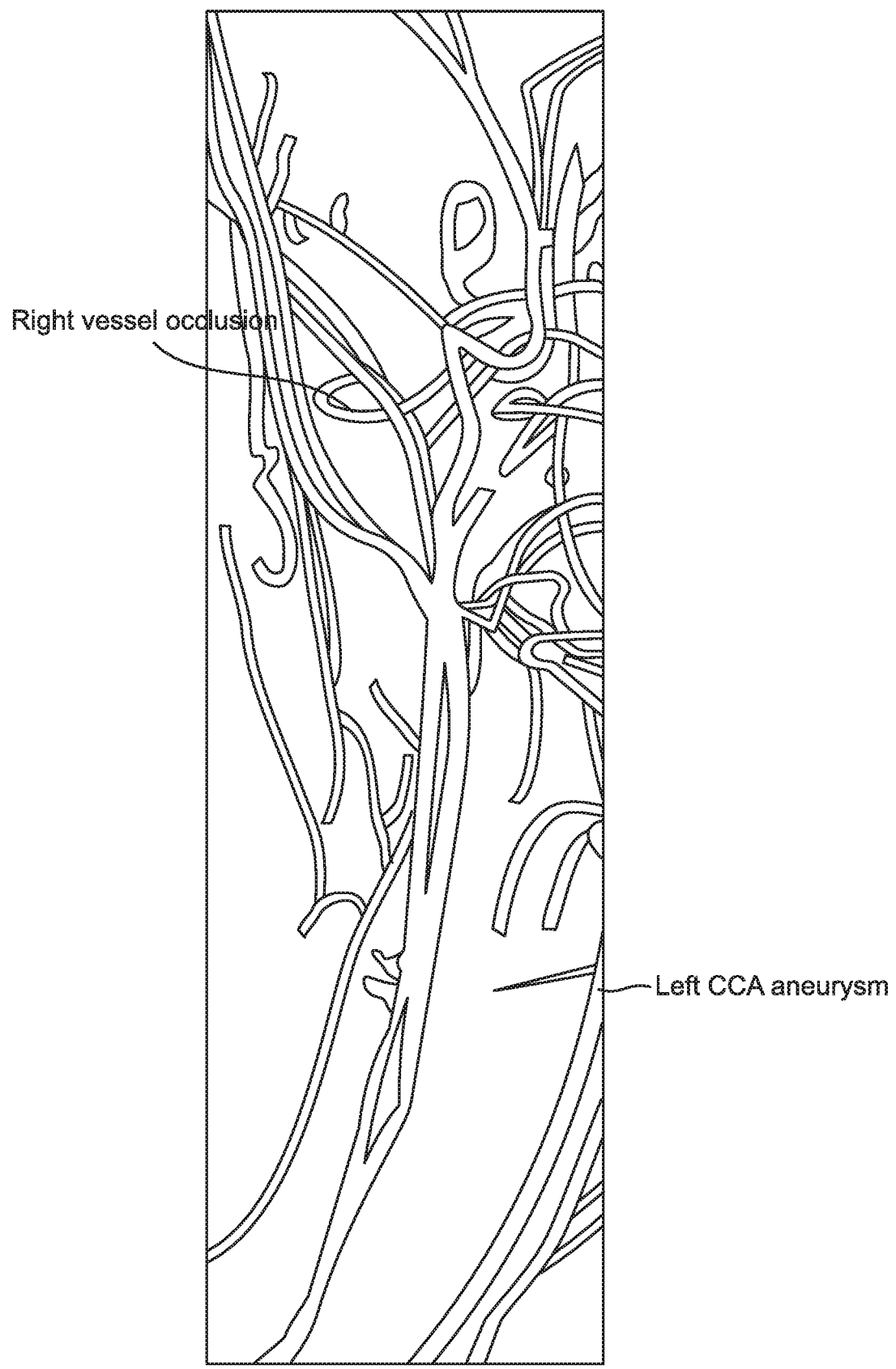
FIG. 17 shows left aneurysm and right vessel occlusion, contrast enhanced (MIP).

FIG. 17 shows left aneurysm and right vessel occlusion, contrast enhanced (MIP).

Data Interpretation:

Susceptibility artifact is highest immediately following coil embolization, and gradually decreases after one-week. The coil system using 304V and platinum metal alloy had an unacceptable artifact, more than 2-fold increase in OEF as compared to the other coil systems tested. This artifact obscured adjacent vascular structures, and is not acceptable for the purpose to follow 304V and platinum coiled aneurysms with MR based angiography techniques. The 35N LT and platinum coil system was slightly better than historical controls (Target and GDC) post-implant in terms of susceptibility artifact. At subsequent follow-up time points, the OEF of the 35N LT and platinum was similar to historical data for the Target and GDC coil systems, indicating an acceptable amount of susceptibility artifact. Notably, the small neck remnant of the aneurysm coiled with the 35N LT and platinum coil system could be seen on short TE TOF MRA, indicating clinically relevant diagnostic quality of the MRA.

Appendix 1: Raw OEF data for each time point

TABLE E5

Artifact volume measurement immediately following implantation (mm 3)

| Aneurysm Location | Left | Right |
|---|---|---|
| Coil Type | 35N LT and platinum | 304V and platinum |
| 3DRA | 317 | 116 |
| Sequence 2 | 736.6 | 678 |
| Sequence 3 | 951 | 874.2 |
| Sequence 4 | 1521 | 1147 |
| Sequence 5 | 872.1 | 865.2 |
| Sequence 6 | 467.3 | n/a |

TABLE E6

Calculated OEFs immediately following implantation.

| Aneurysm Location | Left | Right |
|---|---|---|
| Coil Type | 35N LT and platinum | 304V and platinum |
| Sequence 2 | 2.32 | 5.84 |
| Sequence 3 | 3 | 7.54 |
| Sequence 4 | 4.80 | 9.89 |
| Sequence 5 | 2.75 | 7.46 |
| Sequence 6 | 1.47 | n/a |

TABLE E7

Results of artifact volume measurement one week after Implantation (mm 3)

| Aneurysm Location | Left | Right |
|---|---|---|
| Coil Type | 35N LT and platinum | 304V and platinum |
| 3DRA | 320 | 115 |
| Sequence 2 | 650 | 599.52 |
| Sequence 3 | 722.8 | 789.7 |
| Sequence 4 | 1376 | 1180 |
| Sequence 5 | 914.5 | 810.9 |
| Sequence 6 | 356.8 | n/a |

TABLE E8

Calculated OEFs one week following implantation Aneurysm

| Aneurysm Location | Left | Right |
|---|---|---|
| Coil Type | 35N LT and platinum | 304V and platinum |
| Sequence 2 | 2.03 | 5.21 |
| Sequence 3 | 2.26 | 6.87 |
| Sequence 4 | 4.30 | 10.26 |
| Sequence 5 | 2.86 | 7.05 |
| Sequence 6 | 1.11 | n/a |

TABLE E9

Results of artifact volume measurement four weeks after implantation (mm 3)

| Aneurysm Location | Left | Right |
|---|---|---|
| Coil Type | 35N LT and platinum | 304V and platinum |
| 3DRA | 289 | 130 |
| Sequence 2 | 611.4 | 584.3 |
| Sequence 3 | 733.5 | 748.6 |
| Sequence 4 | 1126 | 1139 |
| Sequence 5 | 843.6 | 808.5 |
| Sequence 6 | 348.5 | n/a |

TABLE E10

Calculated OEFs four weeks following implantation

| Aneurysm Location | Left | Right |
|---|---|---|
| Coil Type | 35N LT and platinum | 304V and platinum |
| Sequence 2 | 2.11 | 4.49 |
| Sequence 3 | 2.53 | 5.75 |
| Sequence 4 | 3.89 | 8.76 |
| Sequence 5 | 2.91 | 6.22 |
| Sequence 6 | 1.20 | n/a |

What is claimed is:

1. An embolization device comprising one or more coils configured for delivery into an aneurysm the coils comprising:
 a non-ferromagnetic metal alloy; further comprising:
 a delivery catheter and a stent, wherein the stent has a radiopaque and electropositive coating comprising tantalum, wherein the surface coating is a vapor deposited layer with a thin 5 to 30 micron layer of Tantalum.

* * * * *